United States Patent
Nakagawa

(10) Patent No.: US 6,730,039 B2
(45) Date of Patent: May 4, 2004

(54) ARTERIOSCLEROSIS-DEGREE EVALUATING APPARATUS

(75) Inventor: Tsuneo Nakagawa, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 10/121,658

(22) Filed: Apr. 15, 2002

(65) Prior Publication Data

US 2003/0078508 A1 Apr. 24, 2003

(30) Foreign Application Priority Data

Oct. 24, 2001 (JP) .................................. 2001-325967

(51) Int. Cl.⁷ .................................................. A61B 5/02
(52) U.S. Cl. ...................... 600/485; 600/490; 600/500; 600/483
(58) Field of Search .................. 600/500, 501, 600/502, 503, 481, 483, 485, 490, 492, 493, 494, 495, 496

(56) References Cited

U.S. PATENT DOCUMENTS

| | | | |
|---|---|---|---|
| 5,743,856 A | | 4/1998 | Oka et al. |
| 5,921,936 A | * | 7/1999 | Inukai et al. ............... 600/490 |
| 6,355,000 B1 | | 3/2002 | Ogura |
| 6,440,079 B1 | * | 8/2002 | Ogura et al. ............... 600/492 |
| 6,475,155 B2 | * | 11/2002 | Ogura et al. ............... 600/500 |

FOREIGN PATENT DOCUMENTS

| | | |
|---|---|---|
| DE | 199 60 452 A1 | 8/2001 |
| EP | 0 885 589 A1 | 12/1998 |
| JP | 4-27854 B2 | 5/1992 |
| JP | 8-66377 A | 3/1996 |
| JP | 9-122091 A | 5/1997 |
| JP | 10-305018 A | 11/1998 |
| JP | P3002570 B2 | 11/1999 |
| JP | P3028393 B2 | 2/2000 |
| JP | P2000-316821 | 11/2000 |
| JP | P2001-137203 A | 5/2001 |
| JP | P2001-190506 A | 7/2001 |
| JP | A 2001-190506 | 7/2001 |

* cited by examiner

*Primary Examiner*—Max F. Hindenburg
*Assistant Examiner*—Navin Natnithithadha
(74) *Attorney, Agent, or Firm*—Oliff & Berridge, PLC

(57) ABSTRACT

An arteriosclerosis-degree evaluating apparatus, including a blood-pressure measuring device which iteratively measures a blood pressure value of a living subject, a pulse-wave-propagation-velocity-related-information obtaining device which iteratively obtains, at substantially a same time as a time when the blood-pressure measuring device measures each blood pressure value of the living subject, a piece of pulse-wave-propagation-velocity-related information that is related to a velocity at which a pulse wave propagates through an artery of the subject, and an output device which outputs a change of the pieces of pulse-wave-propagation-velocity-related information iteratively obtained by the pulse-wave-propagation-velocity-related-information obtaining device, relative to a change of the blood pressure values iteratively measured by the blood-pressure measuring device.

11 Claims, 9 Drawing Sheets

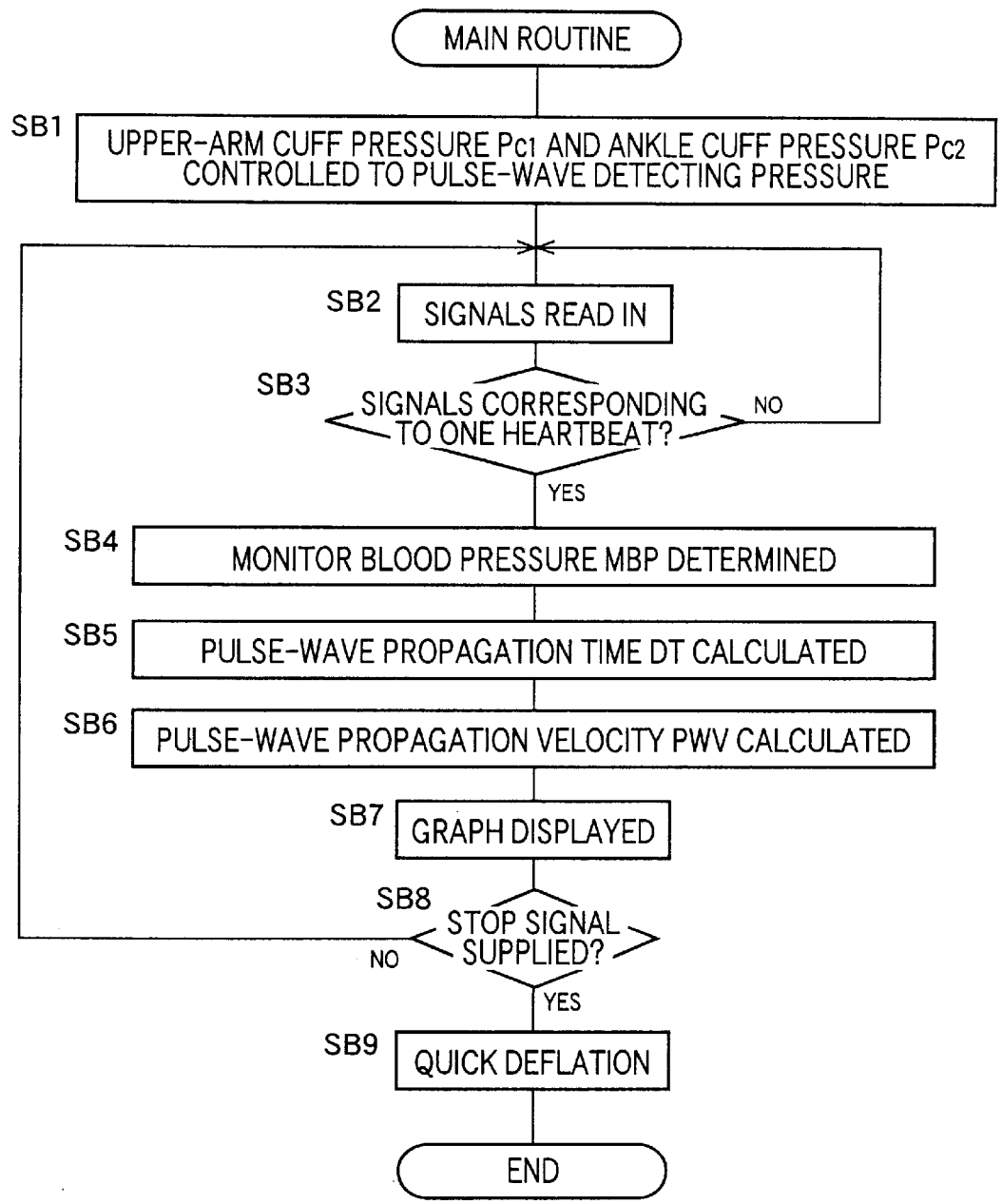

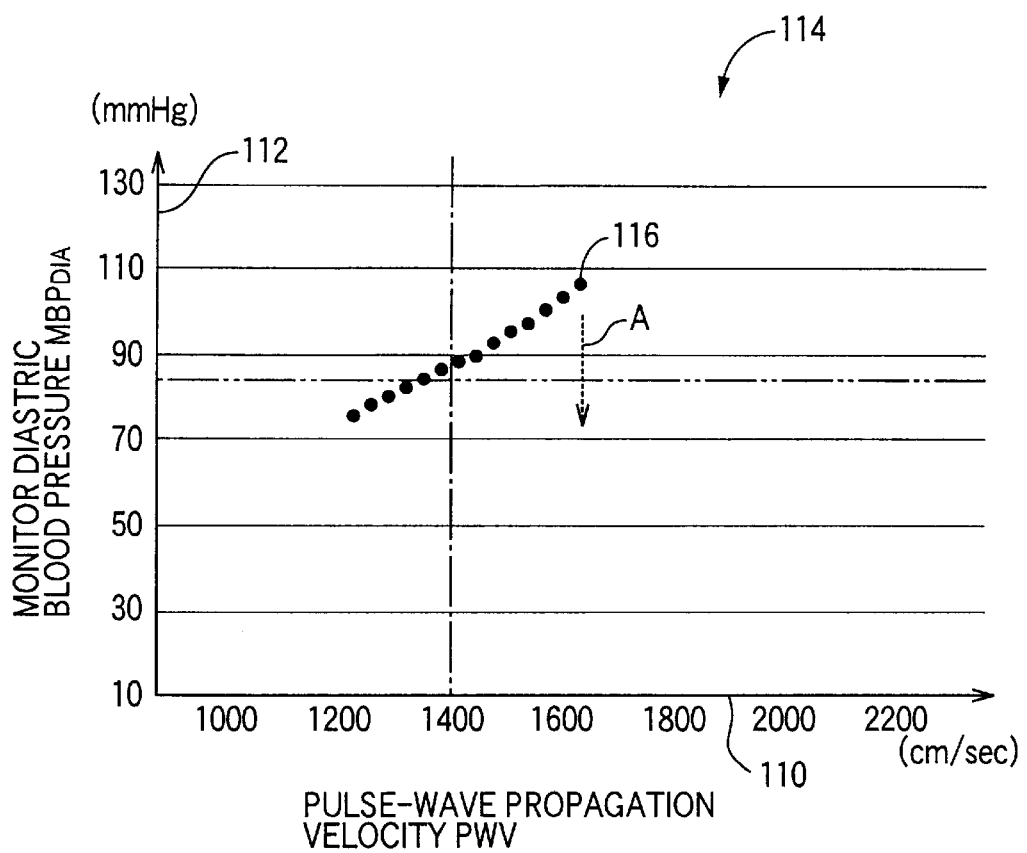

ARTERIOSCLEROSIS-DEGREE EVALUATING APPARATUS

BACKGROUND OF THE INVENTION

1. Field of the Invention

The present invention relates to an arteriosclerosis-degree evaluating apparatus for evaluating an arteriosclerosis degree of a living subject, based on pulse-wave-propagation-velocity-related information that is related to a velocity at which a pulse wave propagates through an artery of the subject; such as a pulse-wave propagation velocity itself, or a pulse-wave propagation time, and particularly relates to an arteriosclerosis-degree evaluating apparatus for evaluating an arteriosclerosis degree based on a change of pulse-wave-propagation-velocity-related information relative to a change of blood pressure.

2. Related Art Statement

The harder a blood vessel is, the faster a pulse wave propagates through the blood vessel. It is therefore known that arteriosclerosis can be diagnosed based on information related to a velocity at which a pulse wave propagates through an artery. It is also known that pulse-wave-propagation-velocity-related information is influenced by blood pressure. For example, it is known that the higher the blood pressure is, the higher the pulse wave propagation velocity is, that is, the lower the blood pressure is, the lower the pulse wave propagation velocity is. Thus, Japanese Patent Document No. 2001-190506 discloses an arteriosclerosis evaluating device which obtains pulse-wave-propagation-velocity-related information, measures blood pressure, and can diagnose an arteriosclerosis degree based on both the obtained information and the measured blood pressure.

However, recently, it has been elucidated that there are cases where though blood pressure changes, pulse-wave propagation velocity does not change so much and, in those very cases, arteriosclerosis has advanced and patents' life expectancy is short. In those cases where pulse-wave propagation velocity does not change so much with blood pressure, it can be said that pulse-wave propagation velocity is so strongly influenced by arteriosclerosis. Thus, it can be said that even if pulse-wave propagation velocity is high and blood pressure is also high, arteriosclerosis has not advanced so much if the velocity lowers as the blood pressure lowers, and that it has advanced if the velocity does not lower so much as the blood pressure lowers.

However, conventionally, the cases where change of pulse-wave propagation velocity relative to change of blood pressure is known have been limited to few cases, e.g., cases where when antihypertensive drug is administered to patients, blood pressure and pulse-wave propagation velocity are measured before and after the administration so as to observe the therapeutic effect of the drug. Even in those cases, a long time is needed before the therapeutic effect appears. Thus, detecting change of pulse-wave propagation velocity relative to change of blood pressure needs a long time.

SUMMARY OF THE INVENTION

It is therefore an object of the present invention to provide an arteriosclerosis-degree evaluating apparatus which can quickly detect change of pulse-wave propagation velocity relative to change of blood pressure.

The above object has been achieved by the present invention. According to the present invention, there is provided an arteriosclerosis-degree evaluating apparatus, comprising a blood-pressure measuring device which iteratively measures a blood pressure value of a living subject; a pulse-wave-propagation-velocity-related-information obtaining device which iteratively obtains, at substantially a same time as a time when the blood-pressure measuring device measures each blood pressure value of the living subject, a piece of pulse-wave-propagation-velocity-related information that is related to a velocity at which a pulse wave propagates through an artery of the subject; and an output device which outputs a change of the pieces of pulse-wave-propagation-velocity-related information iteratively obtained by the pulse-wave-propagation-velocity-related-information obtaining device, relative to a change of the blood pressure values iteratively measured by the blood-pressure measuring device.

The arteriosclerosis-degree evaluating apparatus according to the present invention may be used with a patient whose blood pressure is increasing, e.g., because a physical load is being applied to the patient, or a patient whose blood pressure is decreasing, e.g., because the patient is resting after a physical load has been applied. The blood-pressure measuring device iteratively measures a blood pressure value of the patient, the pulse-wave-propagation-velocity-related-information obtaining device iteratively obtains, at substantially the same time as the time when the blood-pressure measuring device measures each blood pressure value of the patient, a piece of pulse-wave-propagation-velocity-related information, and the output device outputs a change of the pieces of pulse-wave-propagation-velocity-related information iteratively obtained, relative to a change of the blood pressure values iteratively measured. Thus, the present apparatus can quickly detect the change of the pieces of pulse-wave-propagation-velocity-related information, relative to the change of the blood pressure values.

Preferably, the blood-pressure measuring device comprises an inflatable cuff which is adapted to be worn on a portion of the subject; a blood-pressure-value determining means for determining the blood pressure value of the subject based on a signal obtained while a pressure in the cuff is changed; a pressure-pulse-wave detecting device which includes a pressure-pulse-wave sensor that is adapted to be pressed against a prescribed artery of the subject, and which continuously detects, through the pressure-pulse-wave sensor, a pressure pulse wave produced from the prescribed artery; a relationship determining means for determining a relationship between magnitude of pressure pulse wave, and blood pressure, based on at least one blood pressure value measured by the blood-pressure-value determining means and at least one magnitude of the pressure pulse wave detected by the pressure-pulse-wave detecting device; and a blood-pressure monitoring means for iteratively determining, according to the determined relationship, a monitor blood pressure value of the subject, based on a magnitude of each of heartbeat-synchronous pulses of the pressure pulse wave continuously detected by the pressure-pulse-wave detecting device, wherein the pulse-wave-propagation-velocity-related-information obtaining device iteratively obtains a piece of pulse-wave-propagation-velocity-related information at substantially a same time as a time when the blood-pressure monitoring means determines each monitor blood pressure value of the living subject, and wherein the output device outputs a change of the pieces of pulse-wave-propagation-velocity-related information iteratively obtained by the pulse-wave-propagation-velocity-related-information obtaining device, relative to a change of the monitor blood pressure values iteratively determined by the blood-pressure monitoring device.

When the present arteriosclerosis-degree evaluating apparatus is used with a patient whose blood pressure is increasing, or a patient whose blood pressure is decreasing, the blood-pressure monitoring means iteratively determines a monitor blood pressure value of the patient, the pulse-wave-propagation-velocity-related-information obtaining device iteratively obtains a piece of pulse-wave-propagation-velocity-related information at substantially a same time as a time when the blood-pressure monitoring means determines each monitor blood pressure value of the patient, and the output device outputs a change of the pieces of pulse-wave-propagation-velocity-related information iteratively obtained relative to a change of the monitor blood pressure values iteratively determined. Thus, the present apparatus can detect, in more detail, the change of the pieces of pulse-wave-propagation-velocity-related information relative to the change of the monitor blood pressure values, as compared with the case where blood pressure values are iteratively measured using a cuff.

Preferably, the output device displays, in a two-dimensional graph defined by an axis indicative of blood pressure and an axis of pulse-wave propagation velocity, a symbol at a position corresponding to each of the blood pressure values iteratively measured by the blood-pressure measuring device and a corresponding one of the pieces of pulse-wave-propagation-velocity-related information iteratively obtained by the pulse-wave-propagation-velocity-related-information obtaining device.

According to this feature, a medical person such as a doctor or a nurse can visually and easily recognize a change of pulse-wave-propagation-velocity-related information relative to a change of blood pressure, in each of a plurality of time periods; such as a change of pulse-wave-propagation-velocity-related information relative to an initial change of blood pressure, an overall tendency of change of pulse-wave-propagation-velocity-related information relative to change of blood pressure, or a change of pulse-wave-propagation-velocity-related information relative to a terminal change of blood pressure.

Preferably, the pulse-wave-propagation-velocity-related-information obtaining device iteratively obtains the piece of pulse-wave-propagation-velocity-related information that is related to the velocity at which the pulse wave propagates through the artery including an aorta of the subject.

According to this feature, the output device outputs a change of the pieces of pulse-wave-propagation-velocity-related information related to the artery including the aorta, relative to a change of the blood pressure values iteratively measured. The pulse-wave-propagation-velocity-related information related to the artery including the aorta provides an excellent predictive indicator about cardiovascular diseases. Thus, based on the change of pulse-wave-propagation-velocity-related information related to the artery including the aorta, relative to the change of blood pressure values, a medical person can make an accurate diagnosis about the risk of cardiovascular disease.

It is another object of the present invention to provide an arteriosclerosis-degree diagnosing method comprising the step of iteratively obtaining a piece of pulse-wave-propagation-velocity-related information from a patient whose blood pressure is increasing because a prescribed physical load is being applied to the patient, or a patient whose blood pressure is decreasing because the patient is resting after a prescribed physical load has been applied, and the step of diagnosing an arteriosclerosis degree of the patient based on a change of the pieces of pulse-wave-propagation-velocity-related information iteratively obtained.

According to this method, the blood pressure of the patient is changed by applying the physical load to the patient, and the pieces of pulse-wave-propagation-velocity-related information are iteratively obtained from the patient whose blood pressure is increasing because of the physical load, or the patient whose blood pressure is decreasing after the physical load. Thus, a change of the pieces of pulse-wave-propagation-velocity-related information relative to a change of blood pressure can be quickly detected.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 8 is a flow chart representing a main routine which is implemented by the electronic control device shown in FIG. 1 after the routine of FIG. 7; and FIG. 9 is a view showing an example of a two-dimensional graph displayed at Step SB7 shown in FIG. 8.

DETAILED DESCRIPTION OF PREFERRED EMBODIMENTS

Figure 1:
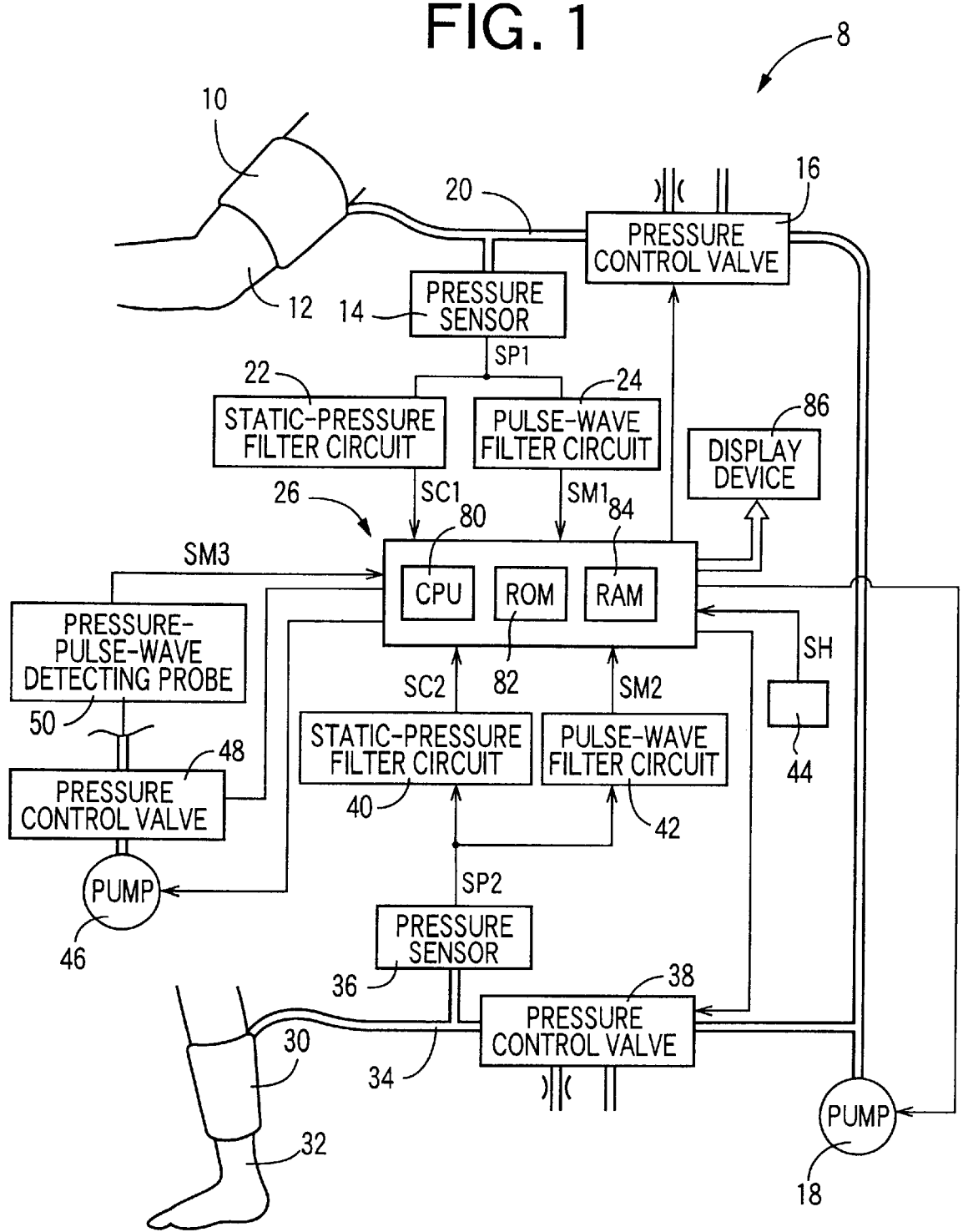
FIG. 1 is a diagrammatic view for explaining a construction of an arteriosclerosis-degree evaluating apparatus to which the present invention is applied.

Hereinafter, there will be described an embodiment of the present invention in detail by reference to the drawings. FIG. 1 shows a diagrammatic view for explaining a construction of an arteriosclerosis-degree evaluating apparatus 8 to which the present invention is applied. This arteriosclerosis-degree evaluating apparatus 8 is used with a patient whose blood pressure is decreasing after having increased because of a prescribed physical load, or a patient whose blood pressure is increasing because of a prescribed physical load. The physical load may be any sort bodily exercise that can increase blood pressure of a patient to some extent; such as an exercise using a treadmill, an exercise using an ergometer, or an exercise using steps. For example, in the case where the treadmill is used, the patient is required to walk on the treadmill at a speed of 40 m/min for five minutes. It is preferred that this evaluating apparatus 8 be used with a patient who is taking a face-up position.

Therefore, in the case where the present apparatus 8 is used with a patient whose blood pressure is increasing, it is preferable to employ a physical load that can be applied to the patient who is taking the face-up position; such as pedaling.

In FIG. 1, reference numeral 10 designates an upper-arm cuff which has a belt-like cloth bag and a rubber bag accommodated in the cloth bag and which is adapted to be wound around, e.g., a right upper arm 12 of a patient as a living subject. The upper-arm cuff 10 is connected to a pressure sensor 14, a pressure control valve 16, and an air pump 18 via a piping 20. The pressure control valve 16 is selectively placed in a pressure-supply position in which the control valve 16 permits a pressurized air to be supplied from the air pump 18 to the cuff 10, a pressure-maintain position in which the control valve 16 maintains a pressure in the cuff 10; a slow-deflation position in which the control valve 16 permits the pressurized air to be slowly discharged from the cuff 10, and a quick-deflation position in which the control valve 16 permits the pressurized air to be quickly discharged from the cuff 10.

The pressure sensor 14 detects an air pressure in the upper-arm cuff 10, and supplies a pressure signal SP1 representing the detected pressure, to each of a static-pressure filter circuit 22 and a pulse-wave filter circuit 24. The static-pressure filter circuit 22 includes a low-pass filter and extracts, from the pressure signal SP1, a static-pressure component contained in the signal SP1, i.e., a cuff-pressure signal SC1 representing a static pressure $Pc_1$ in the upper-arm cuff 10, i.e., a pressing pressure of the cuff 10. The cuff-pressure signal SC1 is supplied to an electronic control device 26 via an A/D (analog-to-digital) converter, not shown. The pulse-wave filter circuit 24 includes a band-pass filter and extracts, from the pressure signal SP1, an oscillating component having predetermined frequencies, i.e., a first cuff-pulse-wave signal SM1. The first cuff-pulse-wave signal SM1 is supplied to the control device 26 via an A/D converter, not shown. The first cuff-pulse-wave signal SM1 represents an upper-arm pulse wave, i.e., a heartbeat-synchronous signal that is produced in synchronism with heartbeat of the patient. Thus, the pulse-wave filter circuit 24 functions as a first heartbeat-synchronous-signal detecting device.

The present apparatus additionally includes an ankle cuff 30 which is adapted to be wound around an ankle 32 of the patient. The ankle cuff 30 is connected to a pressure sensor 36, a pressure control valve 38 via a piping 34. The pressure control valve 38 is connected to the air pump 18, and controls the pressure of the pressurized air supplied from the air pump 18, so that the pressure-controlled air is supplied to the ankle cuff 30. In addition, the control valve 38 controls the pressure in the ankle cuff 30, by deflating the air from the piping 34. The pressure sensor 36 detects the pressure in the ankle cuff 30, and supplies a pressure signal SP2 representing the detected pressure, to each of a static-pressure filter circuit 40 and a pulse-wave filter circuit 42 that have the same constructions as those of the static-pressure filter circuit 22 and the pulse-wave filter circuit 24, respectively. The static-pressure filter circuit 40 extracts, from the pressure signal SP2, a static-pressure component contained in the signal SP2, i.e., a cuff-pressure signal SC2 representing a static pressure $Pc_2$ in the ankle cuff 30, i.e., a pressing pressure of the cuff 30. The cuff-pressure signal SC2 is supplied to the electronic control device 26 via an A/D converter, not shown. The pulse-wave filter circuit 42 extracts, from the pressure signal SP2, an oscillating component having predetermined frequencies, i.e., a second cuff-pulse-wave signal SM2. The second cuff-pulse-wave signal SM2 is supplied to the control device 26 via an A/D converter, not shown. The second cuff-pulse-wave signal SM2 represents an ankle pulse wave, i.e., a heartbeat-synchronous signal that is produced in synchronism with the heartbeat of the patient. Thus, the pulse-wave filter circuit 42 functions as a second heartbeat-synchronous-signal detecting device.

The arteriosclerosis-degree evaluating apparatus 8 additionally includes an input device 44, a pressure-pulse-wave detecting probe 50 functioning as a pressure-pulse-wave detecting device, an air pump 46, and a pressure control valve 48 which controls pressure of a pressurized air supplied from the air pump 46 and supplies the pressure-controlled air to the probe 50. The input device 44 includes a plurality of numeral-input keys, not shown, for inputting a height, H, of the patient, and supplies a height signal SH representing the input patient's height H, to the control device 26.

Figure 2:
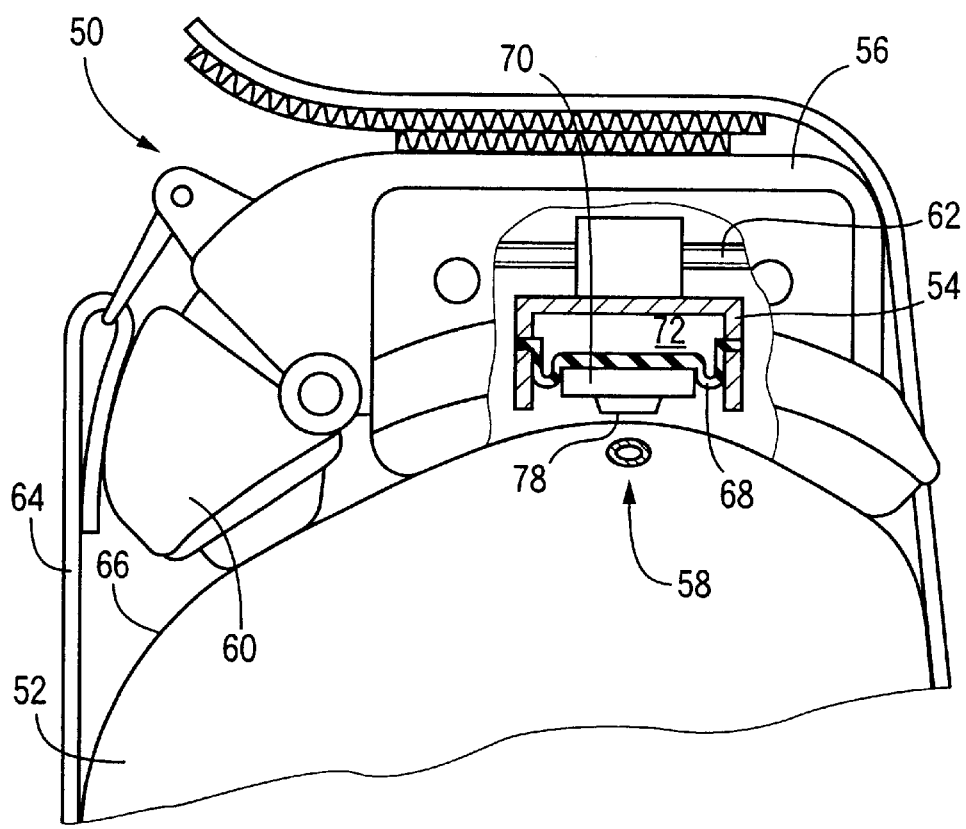
FIG. 2 is a view showing, in detail, a construction of a pressure-pulse-wave detecting probe of the apparatus of FIG. 1.

FIG. 2 shows, in detail, a construction of the pressure-pulse-wave detecting probe 50, which is adapted to be worn on a wrist 52 of the other arm than the arm around which the upper-arm cuff 10 is worn. As shown in FIG. 2, the detecting probe 50 includes a case 56 which accommodates a container-like sensor housing 54; and a feed screw 62 which is threadedly engaged with the sensor housing 54 and is rotated by an electric motor, not shown, provided in a drive section 60 of the case 56 so as to move the sensor housing 54 in a widthwise direction of a radial artery 58. With the help of a fastening band 64 which is connected to the case 56, the case 54 is detachably attached to the wrist 52, such that an open end of the sensor housing 54 is opposed to a body surface 66 of the wrist. In addition, the probe 50 includes a pressure-pulse-wave sensor 70 which is secured via a diaphragm 68 to an inner wall of the sensor housing 54, such that the sensor 70 is movable relative to the housing 54 and is advanceable out of the open end of the same 54. The sensor housing 54, the diaphragm 68, etc. cooperate with one another to define a pressure chamber 72, which is supplied with the pressure-controlled air from the air pump 46 via the pressure-control valve 48 so that the pressure-pulse-wave sensor 70 is pressed against the body surface 66 with a pressing force $P_{HDP}$ corresponding to the air pressure in the pressure chamber 72.

The sensor housing 54 and the diaphragm 66 cooperate with each other to provide a pressing device 74 which presses the pressure-pulse-wave sensor 70 against the radial artery 58, with an optimum pressing force $P_{HDPO}$, described later. The feed screw 62 and the not-shown motor cooperate with each other to provide a pressing-position changing device or a widthwise-direction moving device 76 which moves the pressure-pulse-wave sensor 70 in the widthwise direction of the radial artery 58 and thereby changes a pressing position where the sensor 70 is pressed.

The pressure-pulse-wave sensor 70 includes a semiconductor chip provided by, e.g., a monocrystalline silicon, and having a press surface 78, and a number of semiconductor pressure-sensing elements (not shown) arranged in the press surface 78 at a regular interval of about 0.2 mm in the widthwise direction of the radial artery 58 (i.e., the direction of movement of the sensor 70 parallel to the feed screw 62). The sensor 70 is pressed against the body surface 66 of the wrist 52 right above the radial artery 58, to detect a pressure pulse wave PW(t), i.e., an oscillatory pressure wave which is produced from the radial artery 58 and is propagated to the body surface 66, and supplies a pressure-pulse-wave signal SM3 representing the pressure pulse wave PW(t), to the control device 26 via an A/D converter, not shown.

The electronic control device 26 is provided by a so-called microcomputer including a CPU (central processing unit) 80, a ROM (read only memory) 82, a RAM (random access memory) 84, and an I/O (input-and-output) port, not shown. The CPU 80 processes signals according to the control programs pre-stored in the ROM 82 by utilizing the temporary-storage function of the RAM 84, and outputs drive signals via the I/O port to control the pressure control valves 16, 38, 48 and the air pumps 18, 46. In addition, the CPU 80 processes the signals supplied to the control device 26 so as to iteratively determine monitor blood pressure values MBP and pulse-wave propagation velocity values PWV and control, based on the monitor blood pressure values MBP and the pulse-wave propagation velocity values PWV, a display device 86 to display a change of the velocity values PWV relative to a change of the blood-pressure values MBP.

Figure 3:
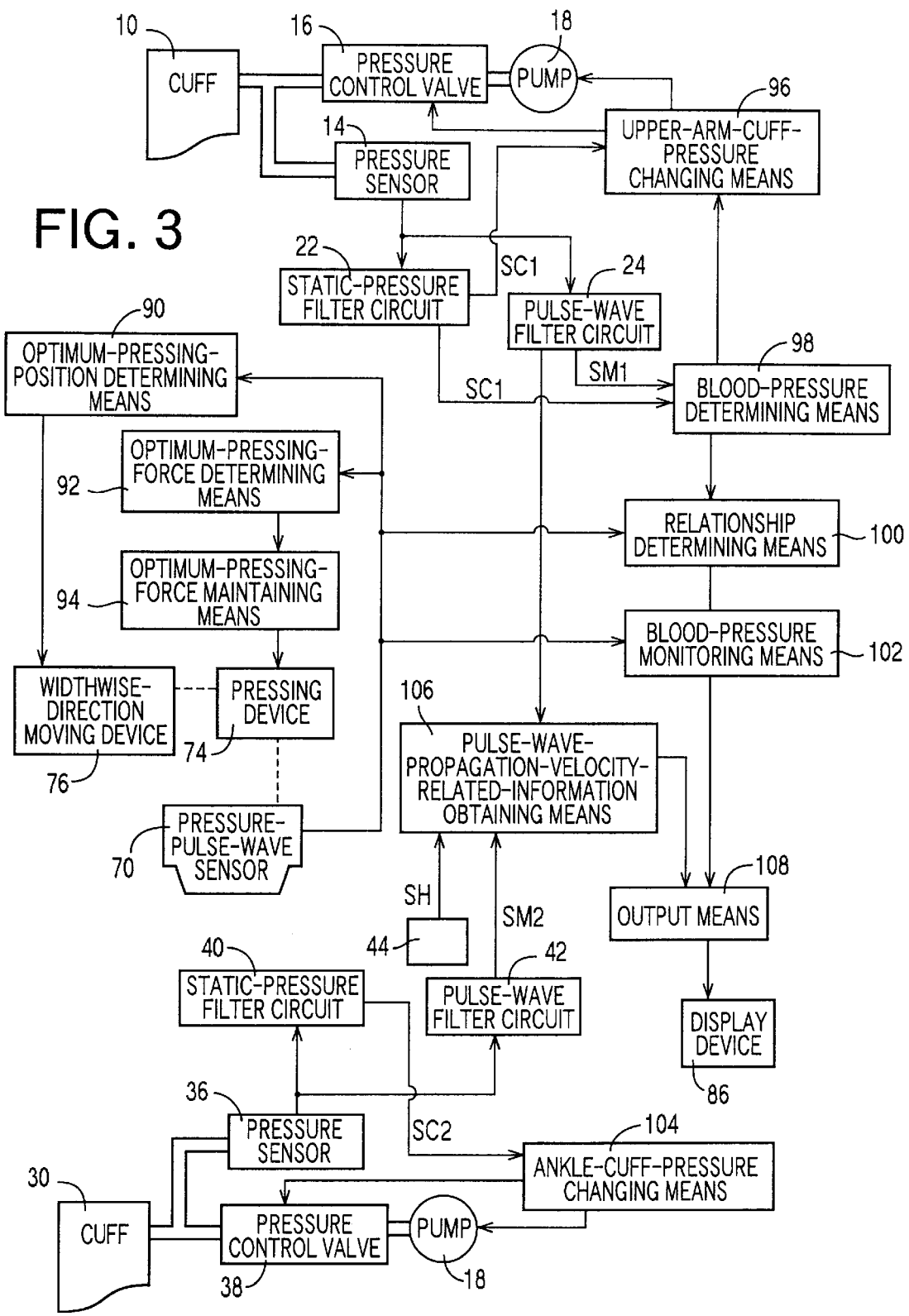
FIG. 3 is a block diagram for explaining essential control functions of an electronic control device of the apparatus of FIG. 1.

FIG. 3 is a block diagram showing essential control functions of the electronic control device 26. In the figure, an optimum-pressing-position determining means 90 operates when the pressure-pulse-wave sensor 70 is initially worn on the patient. First, the determining means 90 operates the pressing device 74 to press the pressure-pulse-wave sensor 70 at a first prescribed pressing pressure $P_1$ which would be sufficiently lower than an optimum pressing pressure $P_{HDPO}$ and, in this state, judges whether one pressure-sensing element that detects the greatest amplitude in all the pressure-sensing elements of the sensor 70 is located in a prescribed central range of the array of pressure-sensing elements. If a negative judgment is made, that is, if the one pressure-sensing element that detects the greatest amplitude is not positioned in the prescribed central range, then the determining means 90 operates the pressing device 74 to move the sensor 70 away from the body surface 66 and operates the moving device 74 to move the sensor 70, and again performs the above-described pressing and judging operations. Meanwhile, if a positive judgment is made indicating that the sensor 70 has been positioned at an optimum pressing position, the determining means 90 determines the pressure-sensing element detecting the greatest amplitude, as a central pressure-sensing element (i.e., an active element), and stores data indicating the pressure-sensing element determined as the active element. Then, the determining means 90 allows an optimum-pressing-force determining means 92 to operate.

Figure 4:
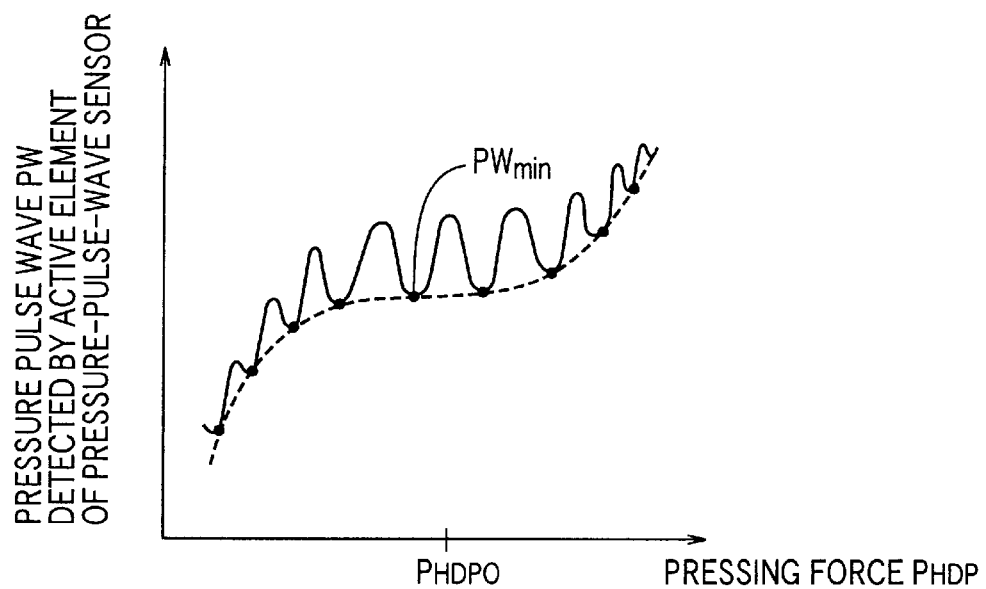
FIG. 4 is a graph for explaining a manner in which an optimum pressing force is determined by an optimum-pressing-force determining means shown in FIG. 3.

The optimum-pressing-force determining means 92 continuously changes the pressing pressure $P_{HDP}$ applied to the pressure-pulse-wave sensor 70 positioned at the optimum pressing position by the optimum-pressing-position determining means 90, and determines an optimum pressing pressure $P_{DHPO}$ based on the pressure pulse wave PW(t) detected by the active element of the sensor 70 during the changing of the pressing pressure $P_{HDP}$. The optimum pressing pressure $P_{DHPO}$ may be determined as follows: First, as shown in a two-dimensional graph shown in FIG. 4, respective minimal values $PW_{min}$ of respective heartbeat-synchronous pulses of the pressure pulse wave PW detected by the active element of the sensor 70 when the pressing pressure $P_{HDP}$ is continuously increased in a pressure range which would include the optimum pressing pressure $P_{DHPO}$, are determined, and then a curve (indicated at broken line in FIG. 4) connecting the respective minimal values $PW_{min}$ of the pressure pulse wave PW is determined. Second, the optimum pressing pressure $P_{DHPO}$ is determined as a pressure which falls within a pressure range which has a prescribed width and whose middle pressure is equal to a middle pressure of a pressure range in which the thus determined curve is substantially horizontal. If the radial artery 58 is pressed by the sensor 70 with the pressure falling within the latter pressure range, a portion of the wall of the artery 58 that is pressed by the sensor 70 is so deformed as to be substantially flat.

Figure 5:
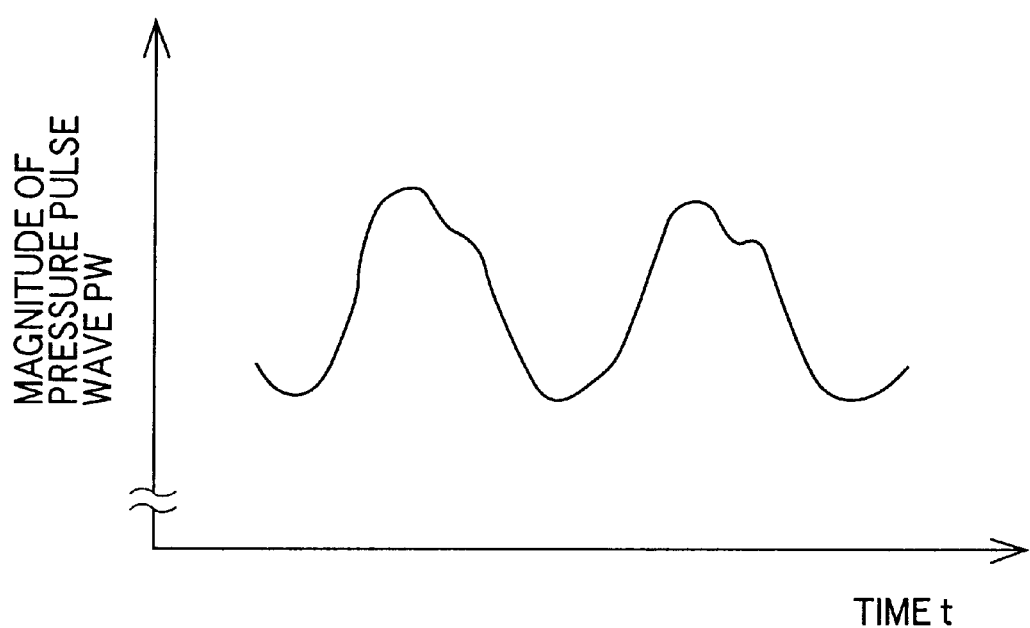
FIG. 5 is a graph showing an example of a pressure pulse wave PW(t) continuously detected by a pressure-pulse-wave sensor in a state in which a pressing force $P_{HDP}$ applied to the pressure-pulse-wave sensor is held at the optimum pressing force $P_{HDPO}$.

An optimum-pressing-force maintaining means 94 operates the air pump 46 and the pressure control valve 48 to maintain the pressing pressure $P_{HDP}$ applied by the pressing device 74 to the pressure-pulse-wave sensor 70, at the optimum pressing pressure $P_{HDPO}$ determined by the optimum-pressing-force determining means 92. FIG. 5 shows two heartbeat-synchronous pulses of a pressure pulse wave PW(t) that are successively detected by the active element of the pressure-pulse-wave sensor 70 in the state in which the pressing pressure $P_{HDP}$ applied to the sensor 70 is maintained at the optimum pressing pressure $P_{HDPO}$.

An upper-arm-cuff-pressure changing means 96 operates the air pump 18 and the pressure control valve 16, in response to a command signal supplied from a blood-pressure determining means 98, described later, and based on the cuff-pressure signal SC1 supplied from the static-pressure filter circuit 22. In response to the command signal supplied from the determining means 98, the changing means 96 operates the air pump 18 and the control valve 16 to quickly increase the pressing pressure of the upper-arm cuff 10, i.e., the cuff pressure $Pc_1$ up to a prescribed target pressure $P_{CM1}$ (e.g., 180 mmHg) which would be higher than an average systolic blood-pressure value $BP_{SYS}$ and subsequently slowly decrease the cuff pressure $Pc_1$ at a rate of from 2 to 3 mmHg/sec. After the blood-pressure determining means 98 determines a blood pressure BP of the patient, the changing means 96 changes the cuff pressure $Pc_1$ to a prescribed upper-arm-pulse-wave detecting pressure. The upper-arm-pulse-wave detecting pressure is defined as a pressure which is sufficiently lower than a diastolic blood pressure of the upper arm 12 and which assures that the first cuff-pulse-wave signal SM1 extracted by the pulse-wave filter circuit 24 has a sufficiently great magnitude. The upper-arm-pulse-wave detecting pressure may be, e.g., 60 mmHg.

The blood-pressure determining means 98 determines a systolic blood pressure value $BP_{SYS}$, a mean blood pressure value $BP_{MEAN}$, and a diastolic blood pressure value $BP_{DIA}$ of the patient, based on the change of the first cuff-pulse-wave signal SM1 obtained while the pressing pressure of the cuff 10 is slowly decreased by the upper-arm-cuff-pressure changing means 96, according to well-known oscillometric method.

Figure 6:
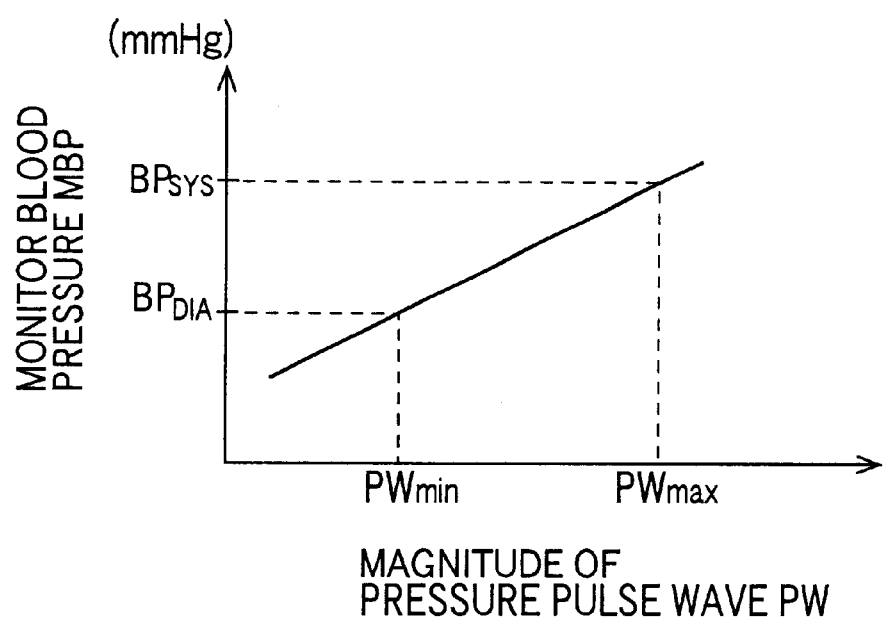
FIG. 6 is a graph showing an example of a relationship determined by a relationship determining means shown in FIG. 3.

A relationship determining means 100 operates the blood-pressure determining means 88 determines, in advance, a relationship between blood pressure and magnitude of pressure pulse wave, based on the blood pressure values BP determined by the blood-pressure determining means 98 and magnitudes of the pressure pulse wave PW detected by the active element of the pressure-pulse-wave sensor 70 at any time in a prescribed time duration consisting of a blood-pressure-measurement period in which the blood pressure values BP are determined by the blood-pressure determining means 98 and respective prescribed time periods preceding and following the blood-pressure-measurement period. FIG. 6 shows an example of the relationship between blood pressure and magnitude of pressure pulse wave. In FIG. 6, symbols $PW_{min}$, $PW_{max}$ indicate a minimal magnitude (i.e., a magnitude of a rising point) and a maximal magnitude (i.e., a magnitude of a peak point) of a heartbeat-synchronous pulse of the pressure pulse wave PW, respectively. The time periods preceding and following the bloodpressure-measurement period are so prescribed that in each of those time periods the blood pressure of the patient does not change so largely from that in the blood-pressure-measurement period, and may include respective time periods immediately before and after the blood-pressure-measurement period.

A blood-pressure monitoring means 102 successively determines, according to the relationship between blood pressure and magnitude of pressure pulse wave, determined by the relationship determining means 100, a monitor blood pressure value MBP of the patient based on a magnitude of each (or every second, third, . . . or n-th one) of respective heartbeat-synchronous pulses of the pressure pulse wave PW detected by the active element of the pressure-pulse-wave sensor 70. More specifically described, the monitoring means 102 successively determines, according to the relationship between blood pressure and pressure-pulse-wave magnitude, a monitor diastolic blood pressure value $MBP_{DIA}$ of the patient based on a minimal magnitude $PW_{min}$ of the pressure pulse wave PW, and successively determines, according to the relationship, a monitor systolic blood pressure $MBP_{SYS}$ of the patient based on a maximal magnitude $PW_{max}$ of the pressure pulse wave PW. In the present arteriosclerosis-degree evaluating apparatus 8, the cuff 10, the blood-pressure determining means 98 which determines the blood pressure value BP based on the signal obtained from the cuff 10, the pressure-pulse-wave detecting probe 50, the relationship determining means 100, and the blood-pressure monitoring means 102 cooperate with one another to provide a blood-pressure measuring device 103.

An ankle-cuff-pressure changing means 104 controls the air pump 18 and the pressure control valve 38 to change and maintain the pressing pressure of the ankle cuff 30, i.e., the cuff pressure Pc2 to and at a prescribed ankle-pulse-wave detecting pressure. The ankle-pulse-wave detecting pressure is defined as a pressure which is sufficiently lower than a diastolic blood pressure of the ankle 32 and which assures that the second cuff-pulse-wave signal SM2 extracted by the pulse-wave filter circuit 42 has a sufficiently great magnitude. Like the upper-arm-pulse-wave detecting pressure, the ankle-pulse-wave detecting pressure may be, e.g., 60 mmHg.

A pulse-wave-propagation-velocity-related information obtaining means 106 successively obtains a piece of pulse-wave-propagation-velocity-related information, in synchronism with each (or every second, third, . . . , n-th one) of successive heartbeats of the patient, based on the first cuff-pulse-wave signal SM1 extracted by the pulse-wave filter circuit 24 and the second cuff-pulse-wave signal SM2 extracted by the pulse-wave filter circuit 42. More specifically described, the obtaining means 106 successively calculates, as a pulse-wave propagation time DT (sec), a time difference between a time of occurrence of a prescribed point (e.g., a rising point or a peak point) of the upper-arm pulse wave represented by the first cuff-pulse-wave signal SM1 continuously extracted by the pulse-wave filter circuit 24 and a time of occurrence of a prescribed point (corresponding to the prescribed point of the upper-arm pulse wave) of the ankle pulse wave represented by the second cuff-pulse-wave signal SM2 continuously extracted by the pulse-wave filter circuit 42. Since the thus calculated pulse-wave propagation time DT is a time difference between a time needed for a pulse wave to propagate from the heart via the aorta to the position where the upper-arm cuff 10 is worn and a time needed for the pulse wave to propagate from the heart via the aorta to the position where the ankle cuff 30 is worn, the time DT can be said as a time needed for the pulse wave to propagate through a portion of the patient that includes the aorta.

The pulse-wave-propagation-velocity-related information obtaining means 106 may additionally determine a propagation distance L, based on the patient's height H supplied from the input device 44, according to a predetermined relationship between propagation distance L and height H that is represented by the following Expression 1 pre-stored in the ROM 82, and may successively determine a pulse-wave propagation velocity PWV (cm/sec), based on the thus determined pulse-wave propagation time DT, according to the following Expression 2:

$$L=aH+b, \qquad \text{(Expression 1)}$$

where a and b are constants that are experimentally determined.

$$PWV=L/DT \qquad \text{(Expression 2)}$$

An output means 108 outputs, to the display device 86, a change of the pieces of pulse-wave-propagation-velocity-related information that are successively obtained by the pulse-wave-propagation-velocity-related information obtaining means 106, relative to a change of the monitor blood pressure values MBP successively determined by the blood-pressure monitoring means 102. For example, the output means 108 calculates an amount of change, ΔMBP, of the monitor blood pressure values MBP in a predetermined time duration, and an amount of change, ΔPWV, ΔDT, of the pulse-wave-propagation velocity or time values PWV, DT in that time duration, calculates a ratio or slope of one of the two change amounts to the other change amount (i.e., ΔPWV/ΔMBP, ΔDT/ΔMBP, ΔMBP/ΔPWV, ΔMBP/ΔDT), and operates the display device 86 to display the ratio. Alternatively, the output means 108 operates the display device 86 to display, in a two-dimensional graph defined by an axis indicative of monitor blood pressure and an axis indicative of pulse-wave-propagation-velocity-related information, a symbol at a position corresponding to each of the monitor blood pressure values MBP successively determined as described above, and a corresponding one of the pieces of pulse-wave-propagation-velocity-related information successively obtained as described above. Otherwise, the output means 106 may operate the display device 86 to display, in the above-indicated two-dimensional graph, a hysteresis loop defined by each of the monitor blood pressure values MBP successively determined, and a corresponding one of the pieces of pulse-wave-propagation-velocity-related information successively obtained, and/or an area inside the hysteresis loop.

Figure 7:
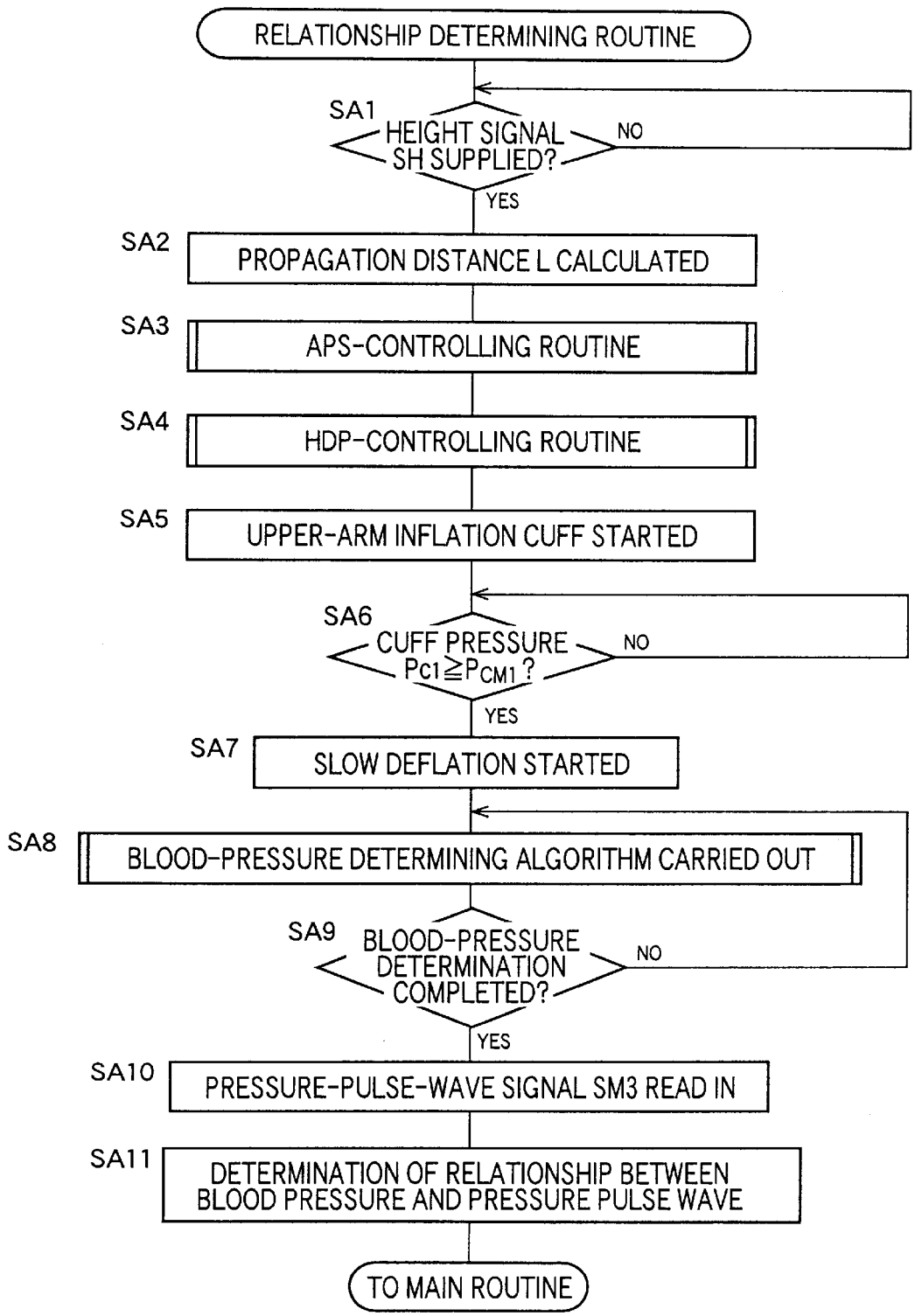
FIG. 7 is a flow chart representing a relationship determining routine which is implemented by the electronic control device shown in FIG. 3 to determine a relationship between pressure pulse wave and blood pressure.

FIGS. 7 and 8 are flow charts representing essential control functions of the electronic control device 26 shown in FIG. 3. FIG. 7 shows a relationship determining routine for determining a relationship between blood pressure and pressure pulse wave; and FIG. 8 shows a main routine that is implemented following the relationship determining routine. Those routines will be described below on the assumption that the present arteriosclerosis-degree evaluating apparatus 8 is used with a patient who has just done a prescribed physical exercise.

First, at Step SA1 (hereinafter, "Step" is omitted, if appropriate), the control device 26 judges whether the height signal SH has been supplied thereto from the input device 44. If a negative judgment is made at SA1, SA1 is repeated till a positive judgment is made. Then, the control goes to SA2 and the following steps. At SA2, the control device calculates a propagation distance L by replacing the parameter L in Expression 1, with the patient's height H represented by the height signal SH supplied from the input device 44.

Subsequently, the control goes to SA3 corresponding to the optimum-pressing-position determining means 90. At SA3, the control device implements an APS-controlling routine. According to this APS-controlling routine, the control device 26 determines an optimum pressing position where one of the pressure-sensing elements of the pressure-pulse-wave sensor 70 that detects the greatest one of the respective amplitudes of the respective pressure pulse waves detected by all the elements, is located at substantially the center of the array of elements. In addition, the control device 26 determines, as an active element, the one pressure-sensing element located at substantially the center of the array of elements.

Subsequently, the control goes to SA4, i.e., an HDP-controlling routine corresponding to the optimum-pressing-force determining means 92 and the optimum-pressing-force maintaining means 94. More specifically described, the control device 26 continuously increases the pressing force $P_{HDP}$ applied to the pressure-pulse-wave sensor 70, and determines, as an optimum pressing force $P_{HDPO}$, a value of the pressing force $P_{HDP}$ at the time when the active element of the sensor 70 detects the greatest one of respective amplitudes of respective heartbeat-synchronous pulses of the pressure pulse wave PW(t). Then, the pressing force $P_{HDP}$ applied to the sensor 70 is maintained at the thus determined optimum pressing force $P_{HDPO}$. In the state in which the pressure-pulse-wave sensor 70 is pressed with the optimum pressing force $P_{HDPO}$, the control device 26 carries out SA5 and the following steps.

At SA5, the control device 26 switches the pressure control valve 16 to its pressure-supply position, and operates the air pump 18, so that the pressure $Pc_1$ in the upper-arm cuff 10 is quickly increased. Then, at SA6, the control device 26 judges whether the cuff pressure $Pc_1$ has reached a prescribed target pressure $P_{CM1}$, i.e., 180 mmHg. If a negative judgment is made at SA6, SA6 is repeated. If a positive judgment is made at SA6, then the control goes to SA7 to stop the air pump 18 and switch the pressure control valve 16 to its slow-deflation position, so that the pressure in the cuff 10 is slowly decreased at a prescribed rate of 3 mmHg/sec.

Then, at SA8 corresponding to the blood pressure determining means 98, the control device 26 determines a systolic blood pressure value $BP_{SYS}$, a mean blood pressure value $BP_{MEAN}$, and a diastolic blood pressure value $BP_{DIA}$ of the patient, based on the change of respective amplitudes of respective heartbeat-synchronous pulses of the upper-arm pulse wave represented by the first cuff-pulse-wave signal SM1 continuously obtained during the slow decreasing of the cuff pressure $Pc_1$, according to a well-known oscillometric-type blood-pressure determining algorithm. Then, at SA9, the control device judges whether the determination of the blood pressure values BP has completed. Since the diastolic blood pressure value $BP_{DIA}$ is last determined at SA8, the control device judges whether the diastolic blood pressure value $BP_{DIA}$ has been determined.

If a positive judgment is made at SA9, then the control goes to SA10 where the control device 26 reads in one pulse of the pressure pulse wave PW represented by the pressure-pulse-wave signal SM3 supplied from the pressure-pulse-wave sensor 70 pressed with the optimum pressing force $P_{HDPO}$, the one pulse corresponding to one heartbeat of the patient. Subsequently, the control goes to SA11 corresponding to the relationship determining means 100. At SA11, the control device 26 determines the relationship between blood pressure and pressure pulse wave, shown in FIG. 6, based on a minimal value $PW_{min}$ and a maximal value $PW_{max}$ of the one heartbeat-synchronous pulse of the pressure pulse wave PW read in at SA10, and the diastolic and systolic blood-pressure values $BP_{DIA}$, $BP_{SYS}$ determined at SA8. SA11 is followed by the main routine shown in FIG. 8.

Next, there will be described the main routine shown in FIG. 8. First, at SB1, the control device again drives the air pump 18, and controls the pressure control valves 16, 38, so as to change and maintain the upper-arm cuff pressure $Pc_1$ and the ankle cuff pressure $Pc_2$, to and at the upper-arm-pulse-wave detecting pressure and the ankle-pulse-wave detecting pressure, respectively, each of which is equal to 60 mmHg.

Then, at SB2, the control device reads in the first cuff-pulse-wave signal SM1 supplied from the pulse-wave filter circuit 24, the second cuff-pulse-wave signal SM2 supplied from the pulse-wave filter circuit 42, and the pressure-pulse-wave signal SM3 supplied from the pressure-pulse-wave sensor 70. Subsequently, at SB3, the control device judges whether it has read in respective one pulses of the first cuff-pulse-wave signal, the second cuff-pulse-wave signal SM2, and the pressure-pulse-wave signal SM3, each of those one pulses corresponding to one heartbeat of the patient. If a negative judgment is made at SB3, SB2 and the following steps are repeated so as to continue reading in those signals.

Meanwhile, if a positive judgment is made at SB3, the control goes to SB4 corresponding to the blood-pressure monitoring means 102. At SB4, the control device determines a minimal value $PW_{min}$ and a maximal value $PW_{max}$ of the one heartbeat-synchronous pulse of the pressure pulse wave PW read in while SB2 and SB3 are repeated, and additionally determines, according to the relationship between blood pressure and pressure pulse wave, determined at SA11 of FIG. 7, a monitor diastolic blood pressure value $MBP_{DIA}$ and a monitor systolic blood pressure value $MBP_{SYS}$ of the patient, based on the minimal value $PW_{min}$ and the maximal value $PW_{max}$.

Then, at SB5, the control device determines respective rising points of the respective one heartbeat-synchronous pulses of the upper-arm and ankle pulse waves read in while SB2 and SB3 are repeated, and determines, as a pulse-wave propagation time DT, a time difference between a time of occurrence of the rising point of the upper-arm pulse wave and a time of occurrence of the rising point of the ankle pulse wave. Next, at SB6, the control device determines a pulse-wave propagation velocity PWV by replacing the variables DT, L in Expression 2, with the pulse-wave propagation time DT determined at SB5 and the subject's height H determined at SA2. Thus, in the flow charts shown in FIGS. 7 and 8, SA2, SB5, and SB6 corresponds to the pulse-wave-propagation-velocity-related-information obtaining means 106.

Subsequently, the control goes to SB7 corresponding to the output means 108. At SB7, as shown in FIG. 9, the control device controls the display device 86 to display, in a two-dimensional graph 114 defined by an axis 110 indicative of pulse-wave propagation velocity and an axis 116 indicative of monitor diastolic blood pressure, a symbol 116 at a position corresponding to the pulse-wave propagation velocity PWV calculated at SB6 and the monitor diastolic blood pressure $MBP_{DIA}$ determined at SB4.

Next, at SB8, the control device judges whether a stop signal has been inputted thereto through operation of a stop switch, not shown. SB2 and the following steps are repeated until a positive judgment is made at SB8. While SB2 and the following steps are repeated, the control device successively determines a monitor blood pressure value MBP and a pulse-wave propagation velocity PWV in synchronism with each heartbeat of the patient, and the display device 86 successively displays a corresponding symbol 116 in the two-dimensional graph 114. Since the symbols 116 are successively displayed, a medical person can recognize, based on a tendency of change of the symbols 116, a change of the pulse-wave propagation velocity values PWV relative to a change of the monitor diastolic blood pressure values $MBP_{DIA}$. If the pulse-wave propagation velocity PWV lowers as the monitor diastolic blood pressure $MBP_{DIA}$ lowers, as shown in FIG. 9, the person can judge that arteriosclerosis is not at an advanced stage. On the other hand, if the pulse-wave propagation velocity PWV does not lower as the monitor diastolic blood pressure $MBP_{DIA}$ lowers, as indicated at arrow, A, in FIG. 9, the person can judge that arteriosclerosis is at an advanced stage. In the two-dimensional graph 114, a two-dot chain line parallel to the pulse-wave-propagation-velocity axis 110 indicates an upper-limit value, 85 mmHg, of a normal range of the monitor diastolic blood pressure $MBP_{DIA}$, and a one-dot chain line parallel to the monitor-diastolic-blood-pressure axis 112 indicates an upper-limit value, 1400 cm/sec, of a normal range of the pulse-wave propagation velocity PWV measured from the upper arm 12 and the ankle 32.

The present arteriosclerosis-degree evaluating apparatus 8 is for displaying the tendency of change of the symbols 116 in the two-dimensional graph 114, and thereby displaying a tendency of change of the pulse-wave propagation velocity PWV relative to the change of the monitor diastolic blood pressure $MBP_{DIA}$. Therefore, when the blood pressure of the patient becomes stable as time elapses after the physical load or exercise, it is not needed any longer to measure the pulse-wave propagation velocity PWV or the monitor diastolic blood pressure $MBP_{DIA}$. Thus, the stop switch, not shown, is operated by the person when the person judges, from the symbols 116 successively displayed in the two-dimensional graph 114, that the monitor diastolic blood pressure values $MBP_{DIA}$ are not longer changing.

If the stop signal is supplied and a positive judgment is made at SB8, the control goes to SB9 where the control device switches the pressure control valves 16, 38 each to the quick-deflation position, and stops the air pump 18, so that the upper-arm cuff pressure $Pc_1$ and the ankle cuff pressure $Pc_2$ are lowered to an atmospheric pressure, and additionally the control device stops the air pump 46 so that the pressing device 74 stops pressing the pressure-pulse-wave sensor 70. In the flow charts shown in FIGS. 7 and 8, SA5 to SA7, SB1, and SB9 correspond to the upper-arm-cuff-pressure changing means 96, and SB1 and SB9 correspond to the ankle-cuff-pressure changing means 104.

In the embodiment in which the flow charts shown in FIGS. 7 and 8 are employed, if the arteriosclerosis-degree evaluating apparatus 8 is used with the patient whose blood pressure is decreasing after the physical load is applied to the patient, the control device 26 determines, at SB4 (the blood-pressure monitoring means 102), a monitor diastolic blood pressure value $MBP_{DIA}$ in synchronism with each heartbeat of the patient, and determines, at SB6 (the pulse-wave-propagation-velocity-related-information obtaining means 106), a pulse-wave propagation velocity PWV, in synchronism with the each heartbeat of the patient, at substantially the same time as the time of determination of the monitor diastolic blood pressure value $MBP_{DIA}$. At SB7 (the output means 108), the control device controls the display device 86 to display, in the two-dimensional graph 114, a symbol 116 at a position corresponding to the monitor diastolic blood pressure value $MBP_{DIA}$ and the pulse-wave propagation velocity PW, each obtained in synchronism with each heartbeat of the patient. Thus, the present apparatus can quickly detect a change of the pulse-wave propagation velocity PWV relative to a change of the monitor diastolic blood pressure value $MBP_{DIA}$, in more detail, as compared with the case where blood pressure values are iteratively measured using a cuff.

In addition, in the embodiment in which the flow charts shown in FIGS. 7 and 8 are employed, the control device 26 controls, at SB7 (the output means 108), the display device 86 to display, in the two-dimensional graph 114 defined by the axis 110 indicative of pulse-wave propagation velocity and the axis 116 indicative of monitor diastolic blood pressure, the symbol 116 at the position corresponding to the pulse-wave propagation velocity PWV calculated at SB6 in synchronism with each heartbeat of the patient and the monitor diastolic blood pressure $MBP_{DIA}$ determined at SB4 in synchronism with the each heartbeat of the patient. Thus, the medical person can visually and easily recognize a change of the pulse-wave propagation velocity PWV relative to a change of the monitor diastolic blood pressure $MBP_{DIA}$, in each of a plurality of time periods; such as a change of the pulse-wave propagation velocity PWV relative to an initial change of the monitor diastolic blood pressure $MBP_{DIA}$, an overall tendency of change of the pulse-wave propagation velocity relative to the change of the monitor diastolic blood pressure $MBP_{DIA}$, or a change of the pulse-wave propagation velocity PWV relative to a terminal change of the monitor diastolic blood pressure $MBP_{DIA}$.

Moreover, in the embodiment in which the flow charts shown in FIGS. 7 and 8 are employed, the pulse-wave propagation velocity PWV calculated at SB4 is a pulse-wave propagation velocity PWV measured from an artery including the aorta of the patient, and the control device controls, at SB7 (the output means 108), the display device 86 to successively display, in the two-dimensional graph 114, the symbols 116 at the respective positions corresponding to the monitor diastolic blood pressure $MBP_{DIA}$ successively determined, and the pulse-wave propagation velocity values PWV successively calculated. In addition, the pulse-wave propagation PWV related to the artery including the aorta provides an excellent predictive indicator about cardiovascular diseases. Thus, based on the tendency of change of the symbols 116 displayed in the two-dimensional graph 114, the medical person can make an accurate diagnosis about the risk of cardiovascular disease.

While the present invention has been described in its preferred embodiments by reference to the drawings, it is to be understood that the invention may otherwise be embodied.

For example, in the illustrated arteriosclerosis-degree evaluating apparatus 8, the blood-pressure measuring device 103 includes, in addition to the upper-arm cuff 10, and the blood-pressure determining means 98 for determining the blood pressure BP based on the signal supplied from the cuff 10, the pressure-pulse-wave detecting probe 50, the relationship determining means 100, and the blood-pressure monitoring means 102; and the output means 108 utilizes the monitor blood pressure values MBP successively determined by the blood-pressure monitoring means 102. However, the output means 108 may utilize the blood pressure values BP determined by the blood-pressure determining means 98. In the latter case, it is possible to omit the pressure-pulse-wave detecting probe 50, the relationship determining means 100, and the blood-pressure monitoring means 102, whereby the upper-arm cuff 10, the pressure sensor 14, the static-pressure filter circuit 22, the pulse-wave filter circuit 24, and the blood-pressure determining means 98 may cooperate with one another to provide the blood-pressure measuring device.

In the above-indicated case where the output means 108 utilizes the blood pressure values BP determined by the blood-pressure determining means 98, the blood-pressure determining means 98 may iteratively determine a blood pressure value (e.g., at every two minutes), and the pulse-wave-propagation-velocity-related-information obtaining means 106 iteratively obtains a piece of pulse-wave-propagation-velocity-related information at substantially the same time as the time when the blood-pressure determining means 98 determines each blood pressure value. Here, the phrase "substantially the same time" means a time duration including, in addition to an accurate time when the blood-pressure determining means 98 determines each blood pressure value, respective times that are immediately before and after the accurate time and when the blood pressure of the patient does not change so much.

Although the above-described blood-pressure determining means 98 determines the blood pressure value BP based on the change of pressure in the upper-arm cuff 10 worn on the upper arm 12, it is possible to determine a blood pressure BP based on change of pressure in the ankle cuff 30 worn on the ankle 32, or it is possible to employ a cuff adapted to be worn on a portion of the patient (e.g., a femoral portion) other than the upper arm 12 or the ankle 32 and determine a blood pressure BP based on change of pressure in that cuff.

In the graph shown in FIG. 9, it is possible to replace the monitor diastolic blood pressure $MBP_{DIA}$ with monitor systolic blood pressure $MBP_{SYS}$.

In the illustrated the arteriosclerosis-degree evaluating apparatus 8, the two cuffs 10, 30 are worn on the upper arm 12 and the ankle 32, respectively, and the pulse-wave-propagation-velocity-related information is obtained based on the respective heartbeat-synchronous signals (i.e., pulse waves) detected from the upper arm 12 and the ankle 32. However, it is possible to obtain pulse-wave-propagation-velocity-related information based on heartbeat-synchronous signals detected from the heart, the neck portion, a wrist, a tip of a finger, or other portions of the patient.

The arteriosclerosis-degree evaluating apparatus 8 may be used with a patient whose blood pressure is changing because of administration of hypertensive drug or antihypertensive drug, or because of changing of room temperature.

While the present invention has been described in detail in its embodiment by reference to the drawings, it is to be understood that the present invention is not limited to those details of the described embodiment and may be embodied with other changes and improvements that may occur to a person skilled in the art without departing from the spirit and scope of the invention defined in the appended claims.

What is claimed is:

1. An arteriosclerosis-degree evaluating apparatus, comprising:
    a blood-pressure measuring device which iteratively measures a blood pressure value of a living subject;
    a pulse-wave-propagation-velocity-related-information obtaining device which iteratively obtains, at substantially a same time as a time when the blood-pressure measuring device measures each blood pressure value of the living subject, a piece of pulse-wave-propagation-velocity-related information that is related to a velocity at which a pulse wave propagates through an artery of the subject; and
    an output device which outputs a change of the pieces of pulse-wave-propagation-velocity-related information iteratively obtained by the pulse-wave-propagation-velocity-related-information obtaining device, relative to a change of the blood pressure values iteratively measured by the blood-pressure measuring device,
    wherein the output device displays, in a two-dimensional graph defined by an axis indicative of blood pressure and an axis of pulse-wave propagation velocity, a symbol at a position corresponding to each of the blood pressure values iteratively measured by the blood-pressure measuring device and a corresponding one of the pieces of pulse-wave-propagation-velocity-related information iteratively obtained by the pulse-wave-propagation-velocity-related-information obtaining device.

2. An apparatus according to claim 1, wherein the blood-pressure measuring device comprises:
    an inflatable cuff which is adapted to be worn on a portion of the subject;
    a blood-pressure-value determining means for determining the blood pressure value of the subject based on a signal obtained while a pressure in the cuff is changed;
    a pressure-pulse-wave detecting device which includes a pressure-pulse-wave sensor that is adapted to be pressed against a prescribed artery of the subject, and which continuously detects, through the pressure-pulse-wave sensor, a pressure pulse wave produced from the prescribed artery;
    a relationship determining means for determining a relationship between magnitude of pressure pulse wave, and blood pressure, based on at least one blood pressure value determined by the blood-pressure-value determining means and at least one magnitude of the pressure pulse wave detected by the pressure-pulse-wave detecting device; and
    a blood-pressure monitoring means for iteratively determining, according to the determined relationship, a monitor blood pressure value of the subject, based on a magnitude of each of heartbeat-synchronous pulses of the pressure pulse wave continuously detected by the pressure-pulse-wave detecting device,
    wherein the pulse-wave-propagation-velocity-related-information obtaining device iteratively obtains a piece of pulse-wave-propagation-velocity-related information at substantially a same time as a time when the blood-pressure monitoring means determines each monitor blood pressure value of the living subject, and
    wherein the output device outputs a change of the pieces of pulse-wave-propagation-velocity-related information iteratively obtained by the pulse-wave-propagation-velocity-related-information obtaining device, relative to a change of the monitor blood pressure values iteratively determined by the blood-pressure monitoring device.

3. An arteriosclerosis-degree evaluating apparatus, comprising:
    a blood-pressure measuring device which iteratively measures a blood pressure value of a living subject;
    a pulse-wave-propagation-velocity-related-information obtaining device which iteratively obtains, at substantially a same time as a time when the blood-pressure measuring device measures each blood pressure value of the living subject, a piece of pulse-wave-propagation-velocity-related information that is related to a velocity at which a pulse wave propagates through an artery of the subject; and an output device which outputs a change of the pieces of pulse-wave-propagation-velocity-related information iteratively obtained by the pulse-wave-propagation-velocity-related-information obtaining device, relative to a change of the blood pressure values iteratively measured by the blood-pressure measuring device, wherein the pulse-wave-propagation-velocity-related-information obtaining device iteratively obtains the piece of pulse-wave-propagation-velocity-related information that is related to the velocity at which the pulse wave propagates through the artery including an aorta of the subject.

4. An apparatus according to claim 3, wherein the blood-pressure measuring device comprises:

an inflatable cuff which is adapted to be worn on a portion of the subject;

a blood-pressure-value determining means for determining the blood pressure value of the subject based on a signal obtained while a pressure in the cuff is changed;

a pressure-pulse-wave detecting device which includes a pressure-pulse-wave sensor that is adapted to be pressed against a prescribed artery of the subject, and which continuously detects, through the pressure-pulse-wave sensor, a pressure pulse wave produced from the prescribed artery;

a relationship determining means for determining a relationship between magnitude of pressure pulse wave, and blood pressure, based on at least one blood pressure value determined by the blood-pressure-value determining means and at least one magnitude of the pressure pulse wave detected by the pressure-pulse-wave detecting device; and a blood-pressure monitoring means for iteratively determining, according to the determined relationship, a monitor blood pressure value of the subject, based on a magnitude of each of heartbeat-synchronous pulses of the pressure pulse wave continuously detected by the pressure-pulse-wave detecting device, wherein the pulse-wave-propagation-velocity-related-information obtaining device iteratively obtains a piece of pulse-wave-propagation-velocity-related information at substantially a same time as a time when the blood-pressure monitoring means determines each monitor blood pressure value of the living subject, and wherein the output device outputs a change of the pieces of pulse-wave-propagation-velocity-related information iteratively obtained by the pulse-wave-propagation-velocity-related-information obtaining device, relative to a change of the monitor blood pressure values iteratively determined by the blood-pressure monitoring device.

5. An arteriosclerosis-degree evaluating apparatus, comprising:

a blood-pressure measuring device which iteratively measures a blood pressure value of a living subject;

a pulse-wave-propagation-velocity-related-information obtaining device which iteratively obtains, at substantially a same time as a time when the blood-pressure measuring device measures each blood pressure value of the living subject, a piece of pulse-wave-propagation-velocity-related information that is related to a velocity at which a pulse wave propagates through an artery of the subject;

an output device which outputs a change of the pieces of pulse-wave-propagation-velocity-related information iteratively obtained by the pulse-wave-propagation-velocity-related-information obtaining device, relative to a change of the blood pressure values iteratively measured by the blood-pressure measuring device;

a first heartbeat-synchronous signal detecting device which detects a first heartbeat-synchronous signal from a first portion of the subject; and a second heartbeat-synchronous signal detecting device which detects a second heartbeat-synchronous signal from a second portion of the subject, wherein the pulse-wave-propagation-velocity-related-information obtaining device iteratively obtains the piece of pulse-wave-propagation-velocity-related information, based on a time of occurrence of a prescribed periodic point of each of a plurality of heartbeat-synchronous pulses of the first heartbeat-synchronous signal and a time of occurrence of a prescribed periodic point of a corresponding one of a plurality of heartbeat-synchronous pulses of the second heartbeat-synchronous signal.

6. An apparatus according to claim 5, wherein the first heartbeat-synchronous signal detecting device comprises a first cuff which detects, as the first heartbeat-synchronous signal, a first pulse wave produced from an upper arm of the subject as the first portion of the subject.

7. An apparatus according to claim 6, wherein the second heartbeat-synchronous signal detecting device comprises a second cuff which detects, as the second heartbeat-synchronous signal, a second pulse wave produced from an ankle of the subject as the second portion of the subject.

8. An apparatus according to claim 7, wherein the pulse-wave-propagation-velocity-related-information obtaining device determines, as the pulse-wave-propagation-velocity-related information, a pulse-wave propagation time equal to a time difference between the time of occurrence of the prescribed periodic point of the first pulse wave and the time of occurrence of the prescribed periodic point of the second pulse wave.

9. An apparatus according to claim 7, wherein the pulse-wave-propagation-velocity-related-information obtaining device determines a pulse-wave propagation time equal to a time difference between the time of occurrence of the prescribed periodic point of the first pulse wave and the time of occurrence of the prescribed periodic point of the second pulse wave, and determines, as the pulse-wave-propagation-velocity-related information, a pulse-wave propagation velocity by dividing the determined pulse-wave propagation time by a distance difference between a first distance between the heart of the subject and the first portion and a second distance between the heart and the second portion.

10. An apparatus according to claim 9, further comprising:

an input device which is operable for inputting a height of the subject;

a memory device which stores a predetermined relationship between height and distance difference; and means for determining, according to the predetermined relationship between height and distance difference, stored in the memory device, the distance difference between the first and second distances, based on the height of the subject, inputted through the input device.

11. An apparatus according to claim 5, wherein the blood-pressure measuring device comprises:

an inflatable cuff which is adapted to be worn on a portion of the subject;

a blood-pressure-value determining means for determining the blood pressure value of the subject based on a signal obtained while a pressure in the cuff is changed;

a pressure-pulse-wave detecting device which includes a pressure-pulse-wave sensor that is adapted to be pressed against a prescribed artery of the subject, and which continuously detects, through the pressure-pulse-wave sensor, a pressure pulse wave produced from the prescribed artery;

a relationship determining means for determining a relationship between magnitude of pressure pulse wave, and blood pressure, based on at least one blood pressure value determined by the blood-pressure-value determining means and at least one magnitude of the pressure pulse wave detected by the pressure-pulse-wave detecting device; and a blood-pressure monitoring means for iteratively determining, according to the determined relationship, a monitor blood pressure value of the subject, based on a magnitude of each of heartbeat-synchronous pulses of the pressure pulse wave continuously detected by the pressure-pulse-wave detecting device, wherein the pulse-wave-propagation-velocity-related-information obtaining device iteratively obtains a piece of pulse-wave-propagation-velocity-related information at substantially a same time as a time when the blood-pressure monitoring means determines each monitor blood pressure value of the living subject, and wherein the output device outputs a change of the pieces of pulse-wave-propagation-velocity-related information iteratively obtained by the pulse-wave-propagation-velocity-related-information obtaining device, relative to a change of the monitor blood pressure values iteratively determined by the blood-pressure monitoring device.

* * * * *